United States Patent [19]

Siegfried

[11] Patent Number: 5,445,815
[45] Date of Patent: Aug. 29, 1995

[54] DRY SUNSCREEN COMPOSITION

[76] Inventor: Robert W. Siegfried, 3628 Charlotte St., Kansas City, Mo. 64109

[21] Appl. No.: 155,600

[22] Filed: Nov. 22, 1993

[51] Int. Cl.$^6$ .......................... A61K 7/42; A61K 7/44; A61K 9/10
[52] U.S. Cl. ........................................ 424/59; 424/60; 514/938
[58] Field of Search ............................................ 424/59

[56] References Cited

U.S. PATENT DOCUMENTS

| | | | |
|---|---|---|---|
| 3,966,902 | 6/1976 | Chromecek | 424/59 |
| 4,172,122 | 10/1979 | Kubik et al. | 424/59 |
| 4,522,807 | 6/1985 | Kaplan | 424/59 |
| 4,690,825 | 9/1987 | Won | 514/847 |
| 4,724,240 | 2/1988 | Abrutyn | 424/59 |
| 4,855,127 | 8/1989 | Abrutyn et al. | 424/59 |
| 4,880,617 | 11/1989 | Chromecek et al. | 424/59 |
| 5,208,038 | 5/1993 | Gressani et al. | 424/489 |

FOREIGN PATENT DOCUMENTS

| | | | |
|---|---|---|---|
| 2608533 | 9/1976 | Germany | 424/76 |
| 63-243012 | 10/1988 | Japan | A61K 7/00 |

OTHER PUBLICATIONS

Doi, et al, "Microencapsulated ultraviolet light–absorbing agents for cosmetics", 89: 168971d, *Chemical Abstracts*, vol. 89, 1978.

Pola Chemical Industries, Inc., "Cosmetic sunscreens containing resin powder", 97: 1505894, *Chemical Abstracts*, vol. 97, 1982.

Layton, D. G., "Preservation and protection of active substances", 99: 54778x *Chemical Abstracts*, vol. 99, 1983.

Vanlerbergne, et al, "Composition containing aqueous dispersions of lipid Spherules", 91: 96523a, *Chemical Abstracts*, vol. 91, 1978.

Chromecek, et al, "Solid diffusion system for emitting a composition for improving the odor of the air", 85: 178439t, *Chemical Abstracts*, vol. 85, 1976.

Yamaguchi, et al, "Cosmetic materials containing porous polymer gels", 110: 218827m, *Chemical Abstracts*, vol. 110, 1989.

Article entitled "Industrial News", *Happi*, Jan. 1992.

Article entitled "Laboratory and Human Exposure Evaluation of Unique Sunscreen Formulations", J. Soc. Cosmet, Chem., 24, 541–550, Aug. 19, 1973.

Charles Fox, "Sunscreen and Suntan Products: Patent and Literature Update", *Cosmetics & Toiletries*, vol. 102, Mar. 1987.

Robert Y. Lockhead, "Encyclopedia of Polymers and Thickeners for Cosmetics", *Cosmetics & Toiletries*, vol. 103, Dec. 1988.

*Primary Examiner*—Dale R. Ore
*Attorney, Agent, or Firm*—Henderson & Sturm

[57] ABSTRACT

A dry sunscreen composition, including a highly cross-linked polymethacrylate copolymer powder combined with active sunscreen ingredients. The composition includes, by weight percent, about 7.50% octyl methoxycinnamate, 5.00% octyl salicylate 15.00% homosalate, 5.00% menthyl anthranilate, 10.00% octocrylene, 6.00% benzophenone-3, 0.05% propylparaben, 0.05% BHT, 4.49% PVP/eicosene copolymer, 5.75% C12–15 alcohols benzoate, 5.75% octyldodecyl neopentanoate, 10.00% titanium dioxide, 0.15% D&C yellow No. 5 aluminum lake, and 25.26% acrylates copolymer.

5 Claims, 1 Drawing Sheet

Coefficient of Absorbance Comparison
Dry Sunscreen and Westwood 29

Wavelength in Nanometers

I Dry Sunscreen    + Westwood 29

DRY SUNSCREEN COMPOSITION

TECHNICAL FIELD

This invention relates to sunscreen compositions, and more particularly to a dry sunscreen formulation.

BACKGROUND ART

Conventional sunscreen products are lotions employing a carrier generally consisting of a water-based emulsion which serves primarily as an aid in dispersing the active ingredients on the skin. As the carrier, water, evaporates from conventional products, a thin film of active ingredient plus excipient is deposited on the skin. The film left behind on the skin is then the portion of the product which lends protection from ultraviolet radiation. High temperature extremes can cause the emulsion to separate leading to unusable product and often leakage. At low temperature extremes, such as those present in a snow skiing environment, the product may freeze and be unusable. Also, high SpF rated emulsion products typically have a greasy feel and makes it difficult for the user to grip tools or sporting equipment.

Those concerned with these and other problems recognize the need for an improved sunscreen composition.

DISCLOSURE OF THE INVENTION

The present invention provides a dry sunscreen composition, including a highly crosslinked polymethacrylate copolymer powder combined with active sunscreen ingredients. The composition includes, by weight percent, about 7.50% octyl methoxycinnamate, 5.00% octyl salicylate, 15.00% homosalate, 5.00% menthyl anthranilate, 10.00% octocrylene, 6.00% benzophenone-3, 0.05% propylparaben, 0.05% BHT, 4.49% PVP/eicosene copolymer, 5.75% C12–15 alcohols benzoate, 5.75% octyldodecyl neopentanoate, 10.00% titanium dioxide, 0.15% D&C yellow No. 5 aluminum lake, and 25.26% acrylates copolymer.

An object of the present invention is the provision of an improved sunscreen composition.

Another object is to provide a sunscreen composition that is applied as a dry powder.

A further object of the invention is the provision of a sunscreen composition that is not sensitive to high or low temperature extremes.

Still another object is to provide a sunscreen composition having a high concentration of active ingredient.

A still further object of the present invention is the provision of a sunscreen composition that is non-greasy, safe and convenient to use.

BRIEF DESCRIPTION OF THE DRAWINGS

These and other attributes of the invention will become more clear upon a thorough study of the following description of the best mode for carrying out the invention, particularly when reviewed in conjunction with the examples and the drawings wherein.

BEST MODE FOR CARRYING OUT THE INVENTION

Figure 1:
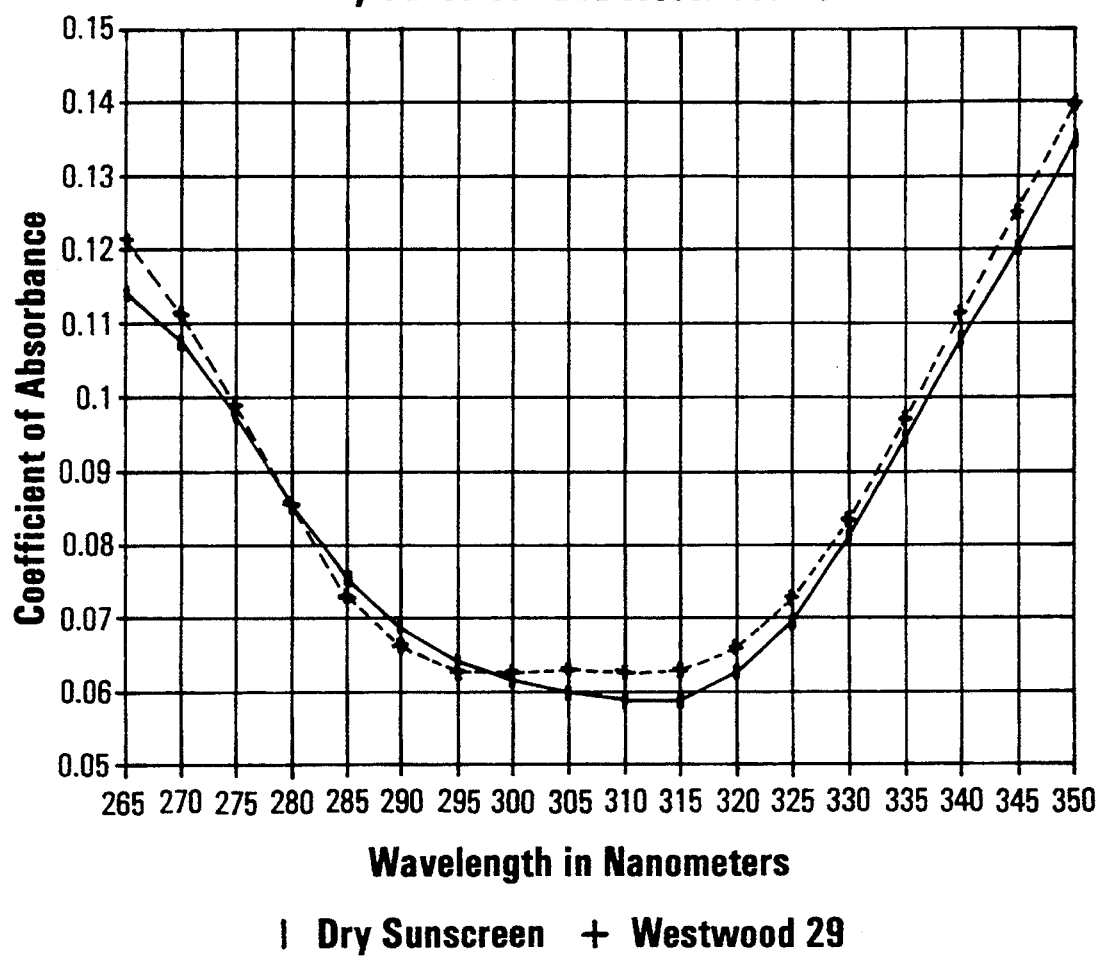
FIG. 1 is a graph illustrating the comparison of coefficients of absorbance for the dry sunscreen of the present invention and a commercially available product.

The following examples are illustrative of the best mode for carrying out the invention. They are obviously not to be construed as limitative of the invention since various other embodiments can readily be evolved in view of the teachings provided herein.

EXAMPLE 1

The dry sunscreen of the present invention is a significant departure from current conventional sunscreen products in that it uses a highly crosslinked polymethacrylate copolymer powder as the application vehicle.

Table 1 provides a positive identification of each of the ingredients used in the dry sunscreen formulation of the present invention. The identification includes the Cosmetic, Toiletry and Fragrance Association (CTFA) name and the Chemical Abstracts Number (CAS#).

TABLE 1

| TRADE NAME/ SUPPLIER | CTFA NAME | DESCRIPTION | CAS # |
| --- | --- | --- | --- |
| N/A | Octyl Methoxycinnamate | 3-(4-Methoxyphenol)-2-Propenoic Acid, 2-Ethylhexyl Ester | 5466-77-3 |
| N/A | Octyl Salicylate | Benzoic Acid, 2-Hydroxy-,2-Ethylhexyl Ester | 118-60-5 |
| N/A | Menthyl Anthranilate | Cyclohexanol, 5-Methyl-2-(1-Methylethyl),-2 Aminobenzoate | 134-09-8 |
| N/A | Homosalate | Benzoic Acid, 2-Hydroxyl-3,3,5-Trimethylcyclohexyl Ester | 118-56-9 |
| N/A | Octocrylene | 2-Ethylhexyl 2 Cyano-3,3-Diphenylacrylate | 6197-30-4 |
| N/A | Benzophenone-3 | 2-Hydroxy-4-Methoxybenzophenone | 131-57-7 |
| N/A | Propylparaben | 4-Hydroxybenzoic Acid, Propyl Ester | 94-13-3 |
| N/A | BHT | 2,6-Bis(1,1-Dimethylethyl)-4-Methylphenol | 128-37-0 |
| Ganex V220 (ISP) | PVP/Eicosene Copolymer | 1-Eicosene, Polymer with 1 Ethenyl-2-Pyrrolidinone | 28211-18-9 |
| Finsolv TN (Finetex Chemicals) | C12–15 Alcohols Benzoate (Patented Material) | Linear Primary Alcohols Benzoate Ester | |
| Elfac I-205 (Alzo Inc.) | Octyldodecyl Neopentanoate (Patent 5,116,604) | | 125496-22-2 |
| Micronized Titanium Dioxide SA-20 (Grant | Titanium Dioxide | Titanium Dioxide | 13463-67-7 |

TABLE 1-continued

DRY SUNSCREEN INGREDIENTS

| TRADE NAME/ SUPPLIER | CTFA NAME | DESCRIPTION | CAS # |
|---|---|---|---|
| Industries) N/A | D&C Yellow No. 5 Aluminum Lake | The aluminum salt of FD&C Yellow No. 5 extended on an appropriate substrate in compliance with 21 CFR 82.1051 | 977058-75-5 |
| Polytrap Q5-6603 (Dow Corning) | Acrylates Copolymer (Patented Material) | | 977069-05-8 |

Table 2 provides a grouping of ingredients into sections and the weight percent of each ingredient. It is to be understood that the typical variation will be at least 0.01% for each ingredient.

TABLE 2

DRY SUNSCREEN FORMULA

| Section | Ingredient | % W/W | 1000 gms |
|---|---|---|---|
| A | Octyl Methoxycinnamate | 7.50 | 75 gm |
| | Octyl Salicylate | 5.00 | 50 gm |
| | Homosalate | 15.00 | 150 gm |
| | Menthyl Anthranilate | 5.00 | 50 gm |
| | Octocrylene | 10.00 | 100 gm |
| | Benzophenone-3 | 6.00 | 60 gm |
| | Proplyparaben | 0.05 | 0.5 gm |
| | BHT | 0.05 | 0.5 gm |
| | Ganex V220 | 4.49 | 44.9 gm |
| B | Finsolu TN | 5.75 | 57.5 gm |
| | Elfac I-205 | 5.75 | 57.5 gm |
| C | Micronized Titanium Dioxide SA-20 | 10.00 | 100 gm |
| | D&C Yellow #5 Aluminum Lake | 0.15 | 1.50 gm |
| D | Polytrap Q5-6603 | 7.70 | 77.00 gm |
| E | Polytrap Q5-6603 | 17.56 | 175.60 gm |

The ingredients are formulated to the finished dry sunscreen composition by the following process steps. Reference to Section A, Section B, etc. relate to the groups of ingredients in Table 2.

1. Combine ingredients in Section A. Heat to 75° C. ±5° C. with constant mixing using a propeller mixer. Mix until clear and homogeneous. Maintain at 75° C. ±5° C. with continuous slow mixing.

2. Combine Section B ingredients. Mix with spatula at ambient temperature.

3. Add Section C ingredients to Section B at ambient temperature. Mix with a spatula to obtain a uniform paste.

4. Add Section CB to Section A. Mix until homogeneous fluid is obtained.

5. Pass Section ABC through a 3-roller mill at 75° C. ±5° C. Remill until a #7 grind on a Hegman gauge is obtained.

6. Return Section ABC to hot bath and reheat to 75° C. ±5° C.

7. Add Section D ingredient to Section ABC. Mix with a propeller mixer while scraping product off the side of the beaker with a spatula.

8. Weight Section E ingredient into a 3000 ml beaker.

9. Remove Section ABCD from heat and gradually add it to Section E continually mixing with a wide spatula.

10. When mixture seems homogeneous stop mixing. Seal beaker with plastic and hold for 24 hours so that absorbance of fluid into resin can be completed.

The advantages offered by the dry sunscreen are significant. Dry sunscreen can be stored indefinitely and at temperature extremes. The esthetics and functionality are not diminished by high or low temperature extremes. This aspect of the dry sunscreen is particularly applicable to the outdoor sports market. Golfers for example, often keep sunscreen products in their golf bag. During storage in automobile trunks and during golfing, the golf bag and sunscreen contained in it are exposed to high temperature extremes. High temperature extremes can, in the case of conventional sunscreen products, cause the emulsion to separate, leading to a non-usable product and often to leakage of the product contents onto equipment being kept in the golf bag. These problems do not occur with the dry sunscreen. At low temperature extremes the benefits of the dry sunscreen are that, unlike most waterbased emulsions, it does not freeze and is usable. Low temperature usability has particular application for snow skiers. In addition to low temperature usability, due to the fact that the dry sunscreen utilizes a powder carrier system, the product will not spill onto ski clothing and equipment as conventional products can. Dry sunscreen, due to the polymer entrapment system used as a delivery vehicle, produces a very dry and non-greasy film on skin. This non-greasy property is important particularly for usage during outdoor sports, and outdoor work applications. The non-greasy characteristic enables users to better maintain their grip on tools and athletic equipment. Dry sunscreen is extremely waterproof due both to its unique carrier system and the composition of the entrapped fluid. Being extremely waterproof, dry sunscreen has particular application for outdoor sports and outdoor work applications. Dry sunscreen is 2 to 2.5 times as concentrated as conventional sunscreen products. The dry copolymer powder carrier system permits high levels of sunscreen active ingredient loading, resulting in a product that requires a lower mg/cc dosage to achieve high SpF. The concentrated nature of the dry sunscreen then results in a light weight product that ships more easily and can be easily stored.

EXAMPLE 2

In clinical SpF evaluations (21 CFR 352.43), the sunscreen test sample is uniformly spread over a 50 cm$^2$ area of the human back. The amount of test sample utilized is sufficient to dose the area at 2 mg/cm$^2$ (or 0.1 gm to the 50 cm$^2$ area). Since the dry sunscreen does not contain a conventional carrier system (water-based emulsion) which evaporates prior to the formation of protective film, it is more concentrated in respect to the sunscreen active ingredients than the type of formula being considered by the test protocol described, as such, a much lower dosage of product would be required. Based on laboratory trials directed at determining the average amount of dry sunscreen that a consumer would apply to a given area of skin, it was determined that a dry sunscreen dosage of 0.80–1.00 mg/cm² would be a reasonable application that would be expected to occur during actual usage (i.e. a 2.5×concentration of active ingredients).

At 0.80–1.00 mg/cm², the dosage of sunscreen active ingredients remaining on the skin is roughly equivalent to the concentrations of sunscreen actives which would be deposited and remain on the skin following volatization of the water base using a conventional, water-based sunscreen lotion of SpF-29 dosed at 2 mg/cm². Active ingredient concentrations can be adjusted to achieve lower SpF values. Correlation of sunscreen active concentration to SpF was based on the attached "Sunscreen Evaluation" results shown in Table 3.

TABLE 3

SUNSCREEN EVALUATION

| WAVE-LENGTH IN NM. | ABSORBANCE DRY SUNSCREEN | COEFFICIENT ABS DRY SUNSCREEN | COEFFICIENT ABS WESTWOOD 29 |
|---|---|---|---|
| 215 |  | 0 | 0 |
| 220 |  | 0 | 0 |
| 225 | 0.0365 | 0.165522 | 0 |
| 230 | 0.3380 | 0.054235 | 0 |
| 235 | 0.3180 | 0.057285 | 0 |
| 240 | 0.2770 | 0.064186 | 0 |
| 245 | 0.1970 | 0.081227 | 0 |
| 250 | 0.1340 | 0.100495 | 0 |
| 255 | 0.1100 | 0.110363 | 0 |
| 260 | 0.1020 | 0.114139 | 0.120955 |
| 265 | 0.1160 | 0.107708 | 0.111281 |
| 270 | 0.1420 | 0.097596 | 0.098664 |
| 275 | 0.1790 | 0.086018 | 0.084913 |
| 280 | 0.2210 | 0.075479 | 0.073266 |
| 285 | 0.2540 | 0.068521 | 0.066212 |
| 290 | 0.2780 | 0.064006 | 0.062939 |
| 295 | 0.2930 | 0.061379 | 0.062413 |
| 300 | 0.3020 | 0.059866 | 0.062763 |
| 305 | 0.3090 | 0.058720 | 0.062588 |
| 310 | 0.3080 | 0.058882 | 0.062763 |
| 315 | 0.2870 | 0.062413 | 0.065838 |
| 320 | 0.2500 | 0.069314 | 0.072196 |
| 325 | 0.1990 | 0.080722 | 0.083036 |
| 330 | 0.1510 | 0.094523 | 0.096897 |
| 335 | 0.1150 | 0.108141 | 0.111746 |
| 340 | 0.0900 | 0.120397 | 0.125665 |
| 345 | 0.0660 | 0.135905 | 0.140670 |
| 350 | 0.0510 | 0.148796 | 0 |
| 355 |  | 0 | 0 |
| 360 |  | 0 | 0 |
| 365 |  | 0 | 0 |
| 370 |  | 0 | 0 |
| 375 |  | 0 | 0 |
| 380 |  | 0 | 0 |
| 385 |  | 0 | 0 |
| 390 |  | 0 | 0 |

Coefficient of correlation between the coefficients of absorbance of Dry Sunscreen and Westwood SPF29 = 0.996007

The evaluation of Table 3 compares the coefficient of absorbance as derived from scanning diluted samples of dry sunscreen and Westwood's SpF 29 lotion in a UV-visible spectrophotometer at 260–345 nanometers. The gm/ml of the dry sunscreen fluid used in the test was reduced by a factor of 2.5 to account for the concentrated nature of the dry sunscreen and the lower dosage requirement.

The coefficient of absorbance is a measure of absorbance which factors into the calculation of the concentration of product in the sample dilution. The coefficient of absorbance calculation is derived from Beers Law and is as follows:

Coefficient of Absorbence = Natural Log (1/Absorbance) (concentrate in gm/ml)

The lower the number generated through the coefficient of absorbance calculation, the greater the blockage of the sample at that wavelength.

The solvent used in preparing diluted samples of test materials was anhydrous methanol. Use of anhydrous methanol as a solvent system causes a slight spectral shift of the data. This shift, however, is a common denominator to all samples.

The graphic representation of the data shown in FIG. 1 and the calculated coefficient of correlation of the coefficient of absorbance (0.996) show that by this test it would be expected that the dry sunscreen will perform as an SpF 25–30 sunscreen when used at the dosage of 0.80–1.00 mg/cm².

Thus it can be seen that all of the stated objectives have been realized.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

I claim:

1. A dry sunscreen composition, consisting essentially of about 7.50 weight percent octyl methoxycinnamate, about 5.00 weight percent octyl salicylate, about 15.00 weight percent homosalate, about 5.00 weight percent menthyl anthranilate, about 10.00 weight percent octocrylene, about 6.00 weight percent benzophenone-3, about 0.05 weight percent propylparaben, about 0.05 weight percent BHT, about 4.49 weight percent PVP/eicosene copolymer, about 5.75 weight percent octyldodecyl neopentanoate, about 5.75 weight percent C12-15 alcohols benzoate, about 10.00 weight percent titanium dioxide, about 0.15 weight percent coloring agent, and about 25.26 weight percent acrylates copolymer, said acrylates copolymer having a formula with the following structure:

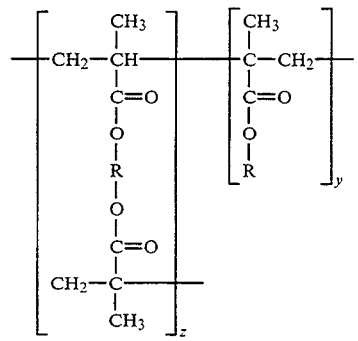

wherein R is alkyl, and x and y are repeating units.

2. A process for preparing a dry sunscreen composition, comprising the steps of:

combining about 7.50 weight percent octyl methoxycinnamate, about 5.00 weight percent octyl salicylate, about 15.00 weight percent homosalate, about 5.00 weight percent menthyl anthranilate, about 10.00 weight percent octocrylene, about 6.00 weight percent benzophenene-3, about 0.05 weight percent propylparaben, about 0.05 weight percent BHT and about 4.49 weight percent PVP/eicosene copolymer to form a first section of ingredients;

heating the first section of ingredients to about 75° C. with constant mixing until it becomes clear and homogenous;

combining about 5.75 weight percent C12-15 alcohols benzoate, and about 5.75 weight percent octyldodecyl neopentanoate to form a second section of ingredients by mixing at ambient temperature;

adding about 10.00 weight percent titanium dioxide, and about 0.15 weight percent coloring agent to the second section of ingredients by mixing at ambient temperature until it becomes a uniform paste;

adding the uniform paste to the first section of ingredients to form a homogenous fluid;

milling the homogenous fluid at about 75° C. until a predetermined size is obtained;

heating the milled homogenous fluid to about 75° C.;

adding about 7.70 weight percent acrylates copolymer to the milled homogenous fluid and mixing to form a third section of ingredients; and adding the third section of ingredients to about 17.56 weight percent acrylates copolymer and mixing until it forms a homogenous dry sunscreen composition, wherein said acrylates copolymer has a formula with the following structure:

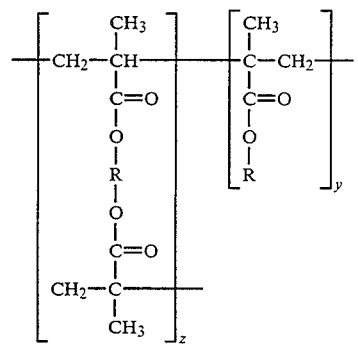

3. The process of claim 2 further including the step of holding the homogenous dry sunscreen composition in a sealed container for twenty-four hours, whereby complete absorbance of the milled homogenous fluid onto the acrylates copolymer is achieved.

4. A dry sunscreen composition produced by the process of claim 2.

5. A dry sunscreen composition produced by the process of claim 3.

* * * * *

UNITED STATES PATENT AND TRADEMARK OFFICE
CERTIFICATE OF CORRECTION

PATENT NO. : 5,445,815
DATED : August 29, 1995
INVENTOR(S) : Siegfried

It is certified that error appears in the above-indentified patent and that said Letters Patent is hereby corrected as shown below:

On the title page, item [57]:

In the Abstract:

in the second to the last line, "dioxode" should read --dioxide--.

Under "Best Mode for Carrying Out the Invention":

in Column 3, lines 40-55, "C." should read --C--.

In the "Claims":

in Column 7, lines 4, 18 and 20, "C." should read --C--;

in Column 8, after the formula diagram in Claim 2, insert the following words --wherein R is alkyl, and x and y are repeating units-- which have been omitted from the claim.

Signed and Sealed this

Twenty-second Day of October, 1996

BRUCE LEHMAN

*Attest:*

*Attesting Officer*     *Commissioner of Patents and Trademarks*